United States Patent
van Duzer et al.

(10) Patent No.: US 10,927,072 B2
(45) Date of Patent: Feb. 23, 2021

(54) PHENYL AND PYRIDINYL HYDROXAMIC ACIDS

(71) Applicant: Acetylon Pharmaceuticals, Inc., Boston, MA (US)

(72) Inventors: John H. van Duzer, Georgetown, MA (US); Ralph Mazitschek, Belmont, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 16/516,747

(22) Filed: Jul. 19, 2019

(65) Prior Publication Data

US 2020/0010407 A1   Jan. 9, 2020

Related U.S. Application Data

(62) Division of application No. 15/807,782, filed on Nov. 9, 2017, now Pat. No. 10,370,324.

(60) Provisional application No. 62/420,291, filed on Nov. 10, 2016.

(51) Int. Cl.

| | |
|---|---|
| *C07C 259/10* | (2006.01) |
| *A61P 25/14* | (2006.01) |
| *A61P 25/28* | (2006.01) |
| *A61P 25/00* | (2006.01) |
| *A61P 25/16* | (2006.01) |
| *A61P 35/00* | (2006.01) |
| *C07D 213/81* | (2006.01) |
| *C07D 309/14* | (2006.01) |
| *C07D 413/12* | (2006.01) |
| *C07D 417/12* | (2006.01) |

(52) U.S. Cl.
CPC ............ *C07C 259/10* (2013.01); *A61P 25/00* (2018.01); *A61P 25/14* (2018.01); *A61P 25/16* (2018.01); *A61P 25/28* (2018.01); *A61P 35/00* (2018.01); *C07D 213/81* (2013.01); *C07D 309/14* (2013.01); *C07D 413/12* (2013.01); *C07D 417/12* (2013.01); *C07C 2601/02* (2017.05); *C07C 2601/14* (2017.05)

(58) Field of Classification Search
CPC .......... A61P 25/00; A61P 25/14; A61P 25/16; A61P 25/28; A61P 35/00; C07C 2601/02; C07C 2601/14; C07D 213/81; C07D 309/14; C07D 413/12; C07D 417/12
See application file for complete search history.

(56) References Cited

U.S. PATENT DOCUMENTS

| | | |
|---|---|---|
| 2008/0207590 A1 | 8/2008 | Deziel et al. |
| 2012/0121502 A1 | 5/2012 | Van Duzer et al. |
| 2015/0105383 A1 | 4/2015 | Quayle et al. |

FOREIGN PATENT DOCUMENTS

| | | |
|---|---|---|
| WO | 2014/181137 A1 | 11/2014 |
| WO | 2015/137750 A1 | 9/2015 |

OTHER PUBLICATIONS

Simoes-Pires (Molecular Neurodegeneration, 2013, p. 1-16). (Year: 2013).*
Dugger, (Cold Spring Harbor Perspectives in Biology, 2017, p. 1-22). (Year: 2017).*
Thomas, J of Neurochemistry, 2018, 145, 96-110 (Year: 2018).*
University of Pittsburg, 2012 (Year: 2012).*
International Search Report with Written Opinion corresponding to International Patent Application No. PCT/US2017/060885, dated Jan. 26, 2018.
Heimburg et al. (J of Medicinal Chem, 2016, 59, 2423-2435, publication date Mar. 3, 2016). (Year: 2016).

* cited by examiner

*Primary Examiner* — Umamaheswari Ramachandran
(74) *Attorney, Agent, or Firm* — Brian C. Trinque; Lathrop GPM LLP

(57) ABSTRACT

The present invention relates to pyrimidine hydroxy amide compounds, the use of such compounds in the inhibition of HDAC6, and the use of such compounds in the treatment of various diseases, disorders, or conditions related to HDAC6.

7 Claims, No Drawings

PHENYL AND PYRIDINYL HYDROXAMIC ACIDS

CROSS-REFERENCE TO RELATED APPLICATIONS

This application is a divisional of U.S. application Ser. No. 15/807,782, filed Nov. 9, 2017, which application claims the benefit of U.S. Provisional Application No. 62/420,291, filed Nov. 10, 2016, the entire content of which is encorporated herein in its entirety.

BACKGROUND

Post-translational modification of proteins through acetylation and deacetylation of lysine residues plays a critical role in regulating a variety of cellular functions, including the control of cell shape, differentiation and proliferation. Histone deacetylases (HDACs) are zinc-binding hydrolases that catalyze the deacetylation of lysine residues on histones as well as non-histone proteins. In particular, HDAC6, a class IIb HDAC, is unique amongst the zinc dependent HDACs in humans. Located in the cytoplasm, HDAC6 has two catalytic domains and an ubiquitin binding domain in its C terminal region. The substrates of HDAC 6 include tubulin, peroxiredoxin, cortactin and heat shock protein 90 (hsp90), but not histones. HDAC6 has been identified as necessary for aggresome formation and for survival of cells following ubiquitinated misfolded protein stress.

There is a need for compounds and methods of using these compounds to treat disorders related to HDAC6 function, including cancers, neurodegenerative disorders, peripheral neuropathies, or polycystic diseases.

SUMMARY

Provided herein are compounds and methods of using these compounds to treat disorders related to HDAC6 function, including cancers, neurodegenerative disorders, peripheral neuropathies, or polycystic diseases.

Thus, in an aspect, provided herein are compounds of Formula I:

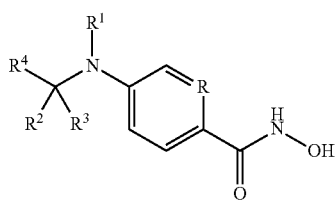

(I)

or pharmaceutically acceptable salts thereof.

Also provided herein is a pharmaceutical composition comprising a compound of Formula I, or a pharmaceutically acceptable salt thereof, together with a pharmaceutically acceptable carrier.

In an aspect, provided herein is a method of inhibiting the activity of HDAC6 in a subject in need thereof, comprising administering to the subject a compound of Formula I, or a pharmaceutically acceptable salt thereof.

In another aspect, provided herein is a method of treating a disease mediated by HDAC6 in a subject in need thereof, comprising administering to the subject a compound of Formula I, or a pharmaceutically acceptable salt thereof.

In another aspect, provided herein is a method of treating cancer in a subject in need thereof, comprising administering to the subject a compound of Formula I, or a pharmaceutically acceptable salt thereof. In an embodiment, the cancer is lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, gliobastoma, hepatocellular carcinoma, papillary renal carcinoma, head and neck squamous cell carcinoma, leukemia, lymphoma, or myeloma. In a further embodiment, the cancer is multiple myeloma.

In another aspect, provided herein is a method of treating a neurodegenerative disorder in a subject in need thereof, comprising administering to the subject a compound of Formula I, or a pharmaceutically acceptable salt thereof. In an embodiement, the neurodegenerative disorder is Alzheimer's disease, Huntington's disease, frontotemporal dementia, progressive supranuclear palsy, cortcobasal dementia, Parkinson's with Lewy-Body dementia, post-traumatic neurodegeneration, or chronic traumatic encephalopathy. In a further embodiement, the neurodegenerative disorder is Alzheimer's disease.

In another aspect, provided herein is a method of treating peripheral neuropathy in a subject in need thereof, comprising administering to the subject a compound of Formula I, or a pharmaceutically acceptable salt thereof. In an embodiment, the peripheral neuropathy is cisplatin-induced peripheral neuropathy, diabetic peripheral neuropathy, Charcot-Marie-Tooth disease, taxol induced neuropathy or vincristine induced neuropathy. In a further embodiment, the compound of Formula I is effective at reversing pain, numbness, tingling, or motor dysfunction.

In yet another aspect, provided herein is a method of treating a polycystic disease in a subject in need thereof, comprising administering to the subject a compound of Formula I, or a pharmaceutically acceptable salt thereof. In an embodiment, the polycystic disease is polycystic liver disease, renal cystic disease, or polycystic kidney disease. In a further embodiment, the compound of Formula I is effective at reducing the growth of cysts.

DETAILED DESCRIPTION

Provided herein are compounds, e.g., the compounds of Formula I or pharmaceutically acceptable salts thereof, that are useful in the treatment of cancers, neurodegenerative disorders, peripheral neuropathies, or polycystic diseases in a subject.

In a non-limiting aspect, these compounds may inhibit histone deacetylases. In a particular embodiment, the compounds provided herein are considered HDAC6 inhibitors. As such, in one aspect, the compounds provided herein are useful in the treatment of cancers, neurodegenerative disorders, peripheral neuropathies, or polycystic diseases in a subject by acting as a HDAC6 inhibitor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated with or caused by the state, disorder or disease being treated. In certain embodiments, the treatment comprises bringing into contact with HDAC6 an effective amount of a compound of the invention for conditions related to cancers, neurodegenerative disorders, peripheral neuropathies, or polycystic diseases.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

The term "jointly therapeutically active" or "joint therapeutic effect" as used herein means that the therapeutic agents can be given separately (in a chronologically staggered manner, especially a sequence-specific manner) in such time intervals that they prefer, in the warm-blooded animal, especially human, to be treated, still show an (preferably synergistic) interaction (joint therapeutic effect). Whether this is the case can, inter alia, be determined by following the blood levels of the compounds, showing that both compounds are present in the blood of the human to be treated at least during certain time intervals.

As used herein, the term "resistant" or "refractive" to a therapeutic agent when referring to a cancer patient means that the cancer has innate, or achieved resistance to, the effects of the therapeutic agent as a result of contact with the therapeutic agent. Stated alternatively, the cancer is resistant to the ordinary standard of care associated with the particular therapeutic agent.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pas.), which is incorporated herein by reference.

The terms "combination," "therapeutic combination," or "pharmaceutical combination" as used herein refer to either a fixed combination in one dosage unit form, or non-fixed combination, or a kit of parts for the combined administration where two or more therapeutic agents may be administered independently, at the same time or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Regardless of whether the active ingredients are administered as a single formulation or in separate formulations, the drugs are administered to the same patient as part of the same course of therapy. In any case, the treatment regimen will provide beneficial effects in treating the conditions or disorders described herein.

The terms "fixed combination," "fixed dose," and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination," "kit of parts," and "separate formulations" means that the active ingredients, i.e., the HDAC6 inhibitor and the aurora kinase inhibitor, are administered to a patient as separate entities either simultaneously, concurrently or sequentially with no specific time limits, wherein such administration provides therapeutically effective levels of the two compounds in the body of the subject in need thereof. The latter also applies to cocktail therapy, e.g., the administration of three or more active ingredients.

An "oral dosage form" includes a unit dosage form prescribed or intended for oral administration. In an embodiment of the pharmaceutical combinations provided herein, the HDAC6 inhibitor (e.g., Compounds A or B) is administered as an oral dosage form. The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl.

As used herein, the term "polycyclic ring" means having two or more carbocyclic rings in which two or more carbons are common to two adjoining rings (the rings are "fused rings") wherein at least one of the rings is aromatic, e.g., the other cyclic rings may be cycloalkyls, and/or aryls. The term "polycyclic ring" includes, but is not limited to, fluorene, anthracene, 9,10-dihydroanthracene, phenanthrene, 9,10-dihydrophenanthrene, phenalene, and 2,3-dihydrophenalene.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

Compounds of the Invention

In an embodiment, provided herein is a compound of Formula I:

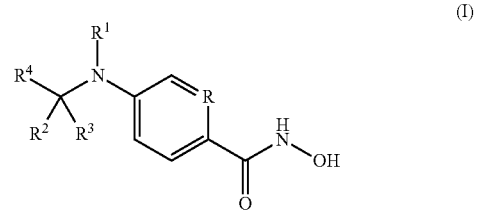

or a pharmaceutically acceptable salt thereof;
wherein
R is C(H) or N;
$R^1$ is H or $C_1$-$C_3$ alkyl;
$R^2$ and $R^3$ are H; or
$R^2$ is H and $R^3$ is aryl, wherein the aryl ring is optionally and independently substituted with 1, 2, or 3 halo, $C_1$-$C_6$ alkyl or $C_1$-$C_6$ alkoxy groups; or
$R^2$ and $R^3$ are taken together to form a $C_3$-$C_6$ cycloalkyl ring or a $C_2$-$C_5$ heterocycloalkyl ring; and
$R^4$ is aryl, wherein the aryl ring is optionally and independently substituted with 1, 2, or 3 halo, $C_1$-$C_6$ alkyl or $C_1$-$C_6$ alkoxy groups; or
$R^3$ is H, and $R^2$ and $R^4$ are taken together to form a polycyclic ring.

In another embodiment, R is C(H) or N;
$R^1$ is H;
$R^2$ and $R^3$ are H; or
$R^2$ is H and $R^3$ is aryl, wherein the aryl ring is optionally and independently substituted with 1, 2, or 3 halo, $C_1$-$C_6$ alkyl or $C_1$-$C_6$ alkoxy groups; and
$R^4$ is aryl, wherein the aryl ring is optionally and independently substituted with 1, 2, or 3 halo, $C_1$-$C_6$ alkyl or $C_1$-$C_6$ alkoxy groups; or
$R^3$ is H, and $R^2$ and $R^4$ are taken together to form a polycyclic ring.

In another embodiment, R is N;
$R^2$ is H and $R^3$ is aryl, wherein the aryl ring is optionally and independently substituted with 1, 2, or 3 halo, $C_1$-$C_6$ alkyl or $C_1$-$C_6$ alkoxy groups; and
$R^4$ is aryl, wherein the aryl ring is optionally and independently substituted with 1, 2, or 3 halo, $C_1$-$C_6$ alkyl or $C_1$-$C_6$ alkoxy groups; or
$R^3$ is H, and $R^2$ and $R^4$ are taken together to form a polycyclic ring.

In another embodiment, $R^2$ is H and $R^3$ is aryl, wherein the aryl ring is optionally and independently substituted with 1, 2, or 3 halo, $C_1$-$C_6$ alkyl or $C_1$-$C_6$ alkoxy groups; and
$R^4$ is aryl, wherein the aryl ring is optionally and independently substituted with 1, 2, or 3 halo, $C_1$-$C_6$ alkyl or $C_1$-$C_6$ alkoxy groups.

In a specific embodiment, including pharmaceutically acceptable salts thereof, Formula I

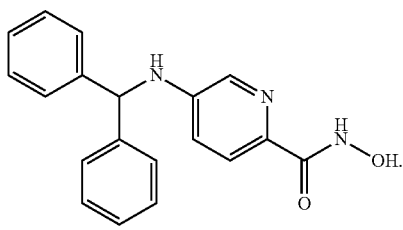 [SMILES: O=C(NO)c1ccc(NC(c2ccccc2)c2ccccc2)cn1]

is:

In another embodiment, $R^3$ is H, and $R^2$ and $R^4$ are taken together to form a polycyclic ring.

In another embodiment, the polycyclic ring is fluorene, anthracene, 9,10-dihydroanthracene, phenanthrene, 9,10-dihydrophenanthrene, phenalene, or 2,3-dihydrophenalene.

In a specific embodiment, including pharmaceutically acceptable salts thereof, Formula I

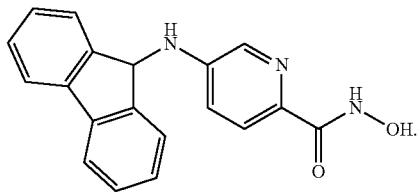 [SMILES: O=C(NO)c1ccc(NC2c3ccccc3-c3ccccc32)cn1]

is:

In another embodiment, R is C(H);
$R^2$ and $R^3$ are H; and
$R^4$ is aryl, wherein the aryl ring is optionally and independently substituted with 1, 2, or 3 halo, $C_1$-$C_6$ alkyl or $C_1$-$C_6$ alkoxy groups.

In another embodiment, $R^4$ is aryl, wherein the aryl ring is optionally and independently substituted with 1, 2, or 3 halo or $C_1$-$C_6$ alkoxy groups.

In a specific embodiment, including pharmaceutically acceptable salts thereof, Formula I

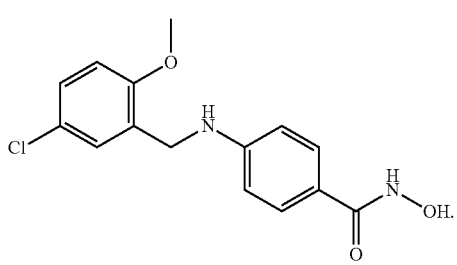 [SMILES: COc1ccc(Cl)cc1CNc1ccc(C(=O)NO)cc1]

is:

Certain embodiments of Formula I, or pharmaceutically acceptable salts thereof, are shown below in Table 1. Compounds of Formula I, or pharmaceutically acceptable salts thereof, and compounds of Table 1, or pharmaceutically acceptable salts thereof, are sometimes referred to herein as "compounds of the invention," or "compounds provided herein."

TABLE 1

| Structure | Compound No. |
|---|---|
| 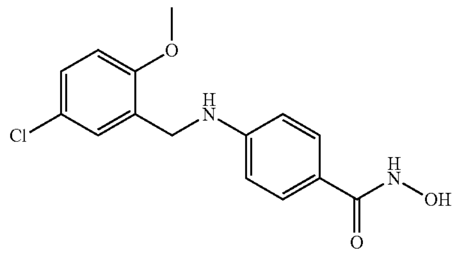 [SMILES: COc1ccc(Cl)cc1CNc1ccc(C(=O)NO)cc1] | 001 |
| 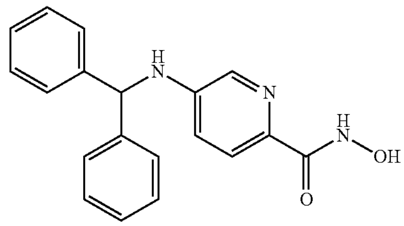 [SMILES: O=C(NO)c1ccc(NC(c2ccccc2)c2ccccc2)cn1] | 002 |
| 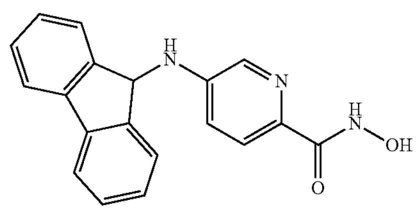 [SMILES: O=C(NO)c1ccc(NC2c3ccccc3-c3ccccc32)cn1] | 003 |
| 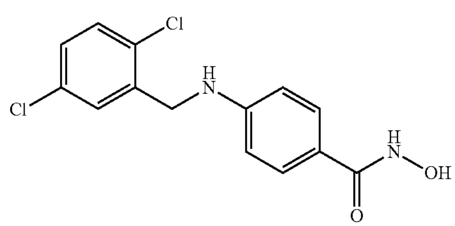 [SMILES: O=C(NO)c1ccc(NCc2cc(Cl)ccc2Cl)cc1] | 004 |
| 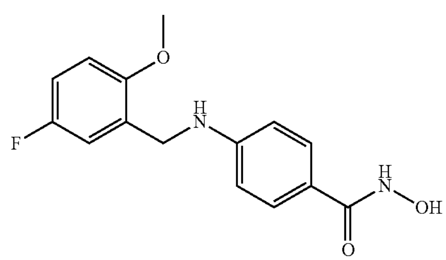 [SMILES: COc1ccc(F)cc1CNc1ccc(C(=O)NO)cc1] | 005 |
| 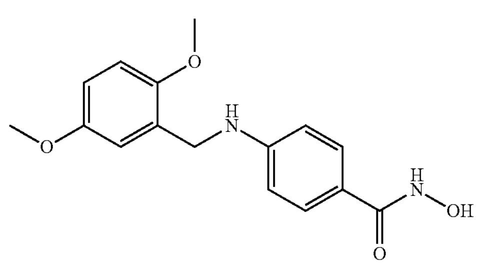 [SMILES: COc1ccc(OC)c(CNc2ccc(C(=O)NO)cc2)c1] | 006 |

TABLE 1-continued
| Structure | Compound No. |
|---|---|
| 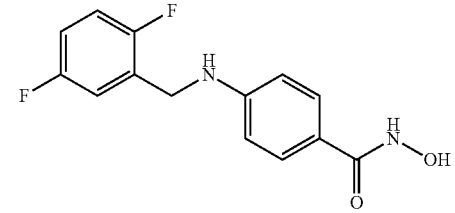 [SMILES: O=C(NO)c1ccc(NCc2cc(F)ccc2F)cc1] | 007 |
| 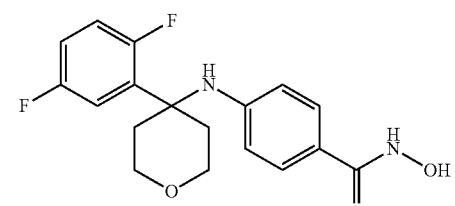 | 008 |
| 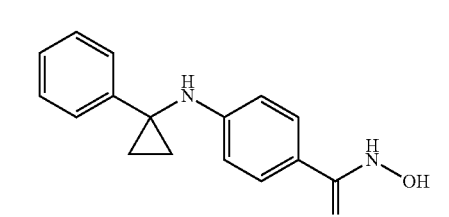 | 009 |
| 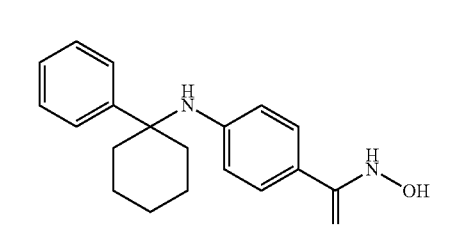 | 010 |
| 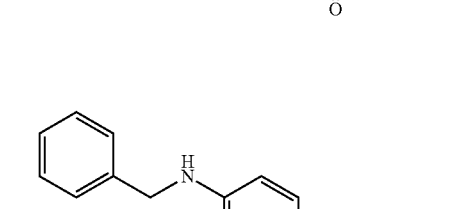 | 011 |
| 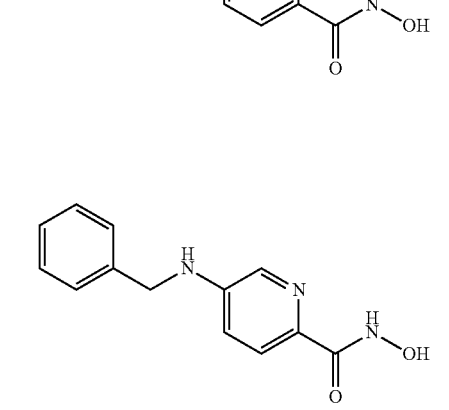 | 012 |
| 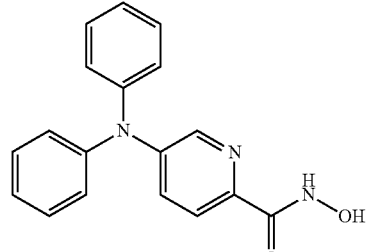 | 013 |
| 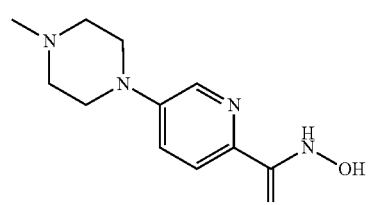 | 014 |
| 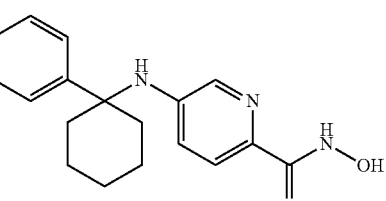 | 015 |
| 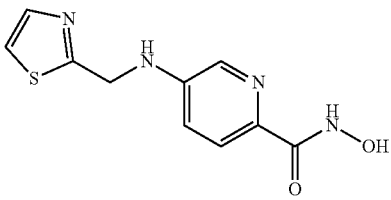 [SMILES: O=C(NO)c1ccc(NCc2ncco2)cn1] | 016 |
| 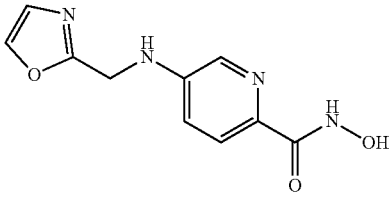 | 017 |
| 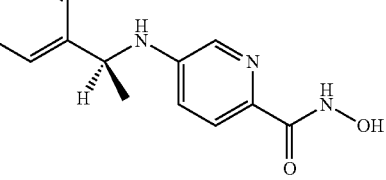 | 018 |
| 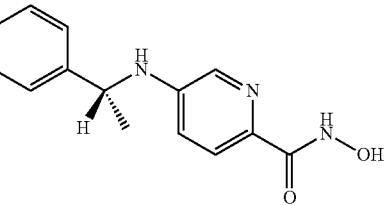 | 019 |

TABLE 1-continued

| Structure | Compound No. |
|---|---|
| [Structure: phenyl-C(CH3)2-NH-pyridine-C(=O)-NH-OH] | 020 |

The disclosed compounds may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of two or more isomers is utilized as the disclosed compound described herein. In another embodiment, a pure isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^2$H (i.e., deuterium) isotope.

In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention.

In one aspect, the invention provides a method of selectively inhibiting HDAC6 over other HDACs (e.g., HDAC1, HDAC2, and HDAC3) in a subject, comprising administering to the subject a compound of Formula I or any of the compounds of Table 1 or pharmaceutically acceptable salts thereof.

In one embodiment, the compound of any of the formulae herein (e.g., formula I) has a selectivity for HDAC6 of 5 to 1000 fold over other HDACs.

In another embodiment, the compound of any of the formulae herein (e.g., formula I) has a selectivity for HDAC6 when tested in a HDAC enzyme assay of about 5 to 1000 fold over other HDACs.

In certain embodiments, the compound has a selectivity for HDAC6 of 15 to 40 fold over other HDACs.

In another aspect, the invention provides a method of treating a disease mediated by HDAC6 in a subject comprising administering to the subject a compound of Formula I or any of the compounds of Table 1.

In certain embodiments, the disease is cancer.

In a further embodiment, the cancer is selected from lung cancer, colon cancer, breast cancer, prostate cancer, liver cancer, brain cancer, kidney cancer, ovarian cancer, stomach cancer, skin cancer, bone cancer, gastric cancer, pancreatic cancer, glioma, gliobastoma, hepatocellular carcinoma, papillary renal carcinoma, head and neck squamous cell carcinoma, leukemia, lymphoma, and myeloma.

In a particular embodiment, the cancer is multiple myeloma.

In another embodiment, the disease is a neurodegenerative disorder.

In a further embodiment, the neurodegenerative disorder is selected from Alzheimer's disease, Huntington's disease, frontotemporal dementia, progressive supranuclear palsy, cortcobasal dementia, Parkinson's with Lewy-Body dementia, post-traumatic neurodegeneration, or chronic traumatic encephalopathy.

In a particular embodiment, the neurodegenerative disorder is Alzheimer's disease.

In another embodiment, the disease is peripheral neuropathy.

In an embodiment, the peripheral neuropathy is cisplatin-induced peripheral neuropathy, diabetic peripheral neuropathy, Charcot-Marie-Tooth disease, taxol induced neuropathy or vincristine induced neuropathy.

In a particular embodiment, the compound of Formula I is effective at reversing pain, numbness, tingling, or motor dysfunction.

In another embodiment, the disease is a polycystic disease.

In a further embodiment, the polycystic disease is polycystic liver disease, renal cystic disease, or polycystic kidney disease.

In a particular embodiment, the compound of Formula I is effective at reducing the growth of cysts.

Preferably, the compound of Formula I is a selective inhibitor of HDAC6 and, as such, is useful in the treatment of disorders modulated by histone deacetylases.

In one embodiment, the compound of Formula I is a selective inhibitor of tubulin deacetylases and, as such, is useful in the treatment of disorders modulated by tubulin deacetylases.

Thus, in another aspect of the invention, methods for the treatment of a disease mediated by HDAC6 are provided comprising administering a therapeutically effective amount of a compound of Formula I, as described herein, to a subject in need thereof. In certain embodiments, the subject is identified as in need of such treatment. In certain embodiments, a method for the treatment of a disease is provided comprising administering a therapeutically effective amount of a compound of Formula I, or a pharmaceutical composition comprising a compound of Formula I to a subject in need thereof, in such amounts and for such time as is necessary to achieve the desired result.

In certain embodiments, the method involves the administration of a therapeutically effective amount of a compound of Formula I or a pharmaceutically acceptable derivative thereof to a subject (including, but not limited to a human or animal) in need of it (including a subject identified as in need).

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

Compounds of the invention can be orally administered in an amount from about 10 mg to about 1000 mg (including e.g., about 10 mg to about 500 mg) per day in single or multiple doses. Thus, in an embodiment of the methods of treatment provided herein, the compound of Formula I is administered at a dosage of about 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, or 500 mg per day. In a further embodiment, the compound of Formula I is administered at a dosage of about 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, or 200 mg per day.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra)nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. The following examples further illustrate aspects of the present invention. However, they are in no way a limitation of the teachings or disclosure of the present invention as set forth

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

Synthesis Procedures

Example 1—Synthesis of Compound 001

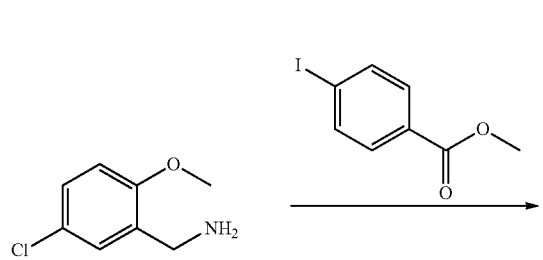

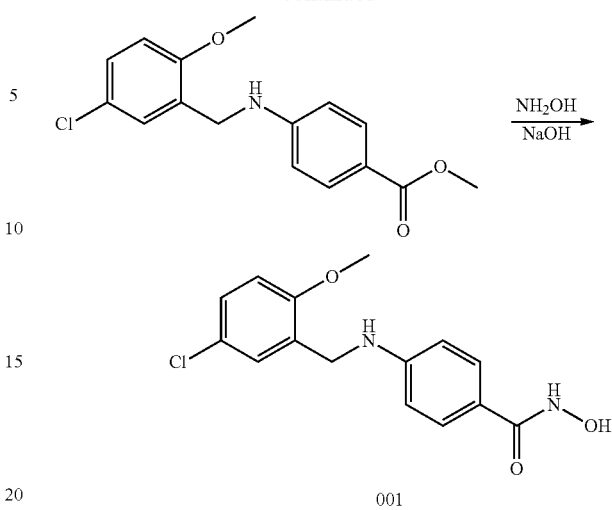

Step 1:

To a solution of (5-chloro-2-methoxyphenyl)-methanamine (200 mg, 1.1 mmol) and methyl 4-iodobenzoate (643 mg, 1.0 mmol), $Pd_2(dba)_3$ (106 mg, 0.11 mmol), Ruphos (54 mg, 0.11 mmol), $CsCO_3$ (759 mg, 2.32 mmol) in toluene (10 ml) under $N_2$ protection. The mixture was stirred at 90° C. overnight. The solution was concentrated and washed with water, then the combined organic layers were washed by water and purified by prep-TLC (PET/EtOAc=3:1) to afford a liquid (160 mg, 44.8%).

Step 2:

To a solution of 4-(5-chloro-2-methoxybenzylamino)benzoate (100 mg, 0.32 mmol) in DCM (1 ml) and MeOH (2 ml) was added NaOH (sat. in MeOH, 1 ml) and $NH_2OH$ (2 ml) at 0° C. The mixture was stirred at 0° C. for 1 h, then the solvent was evaporated off, the residue was extracted by EtOAc (10 ml×2). The combined organic layer was washed with aqueous NaCl, dried by anhydrous $Na_2SO_4$, concentrated in vacuo to afford Compound 001 as a yellow solid (61 mg, 61%). $^1$H NMR (400 MHz, DMSO) δ 10.76 (s, 1H), 8.67 (s, 1H), 7.51 (d, J=8.7 Hz, 2H), 7.27 (dd, J=8.7, 2.7 Hz, 1H), 7.17 (d, J=2.6 Hz, 1H), 7.04 (d, J=8.8 Hz, 1H), 6.66 (t, J=6.2 Hz, 1H), 6.53 (d, J=8.7 Hz, 2H), 4.25 (d, J=6.0 Hz, 2H), 3.83 (d, J=11.4 Hz, 3H). LCMS: m/z=307 (M+H)$^+$.

Example 2—Synthesis of Compound 002

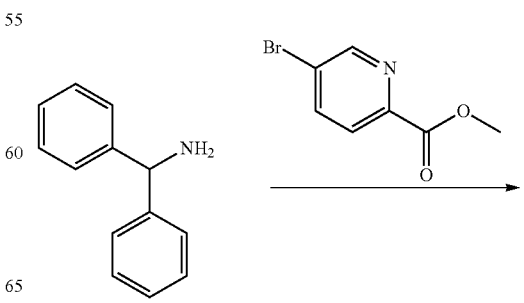

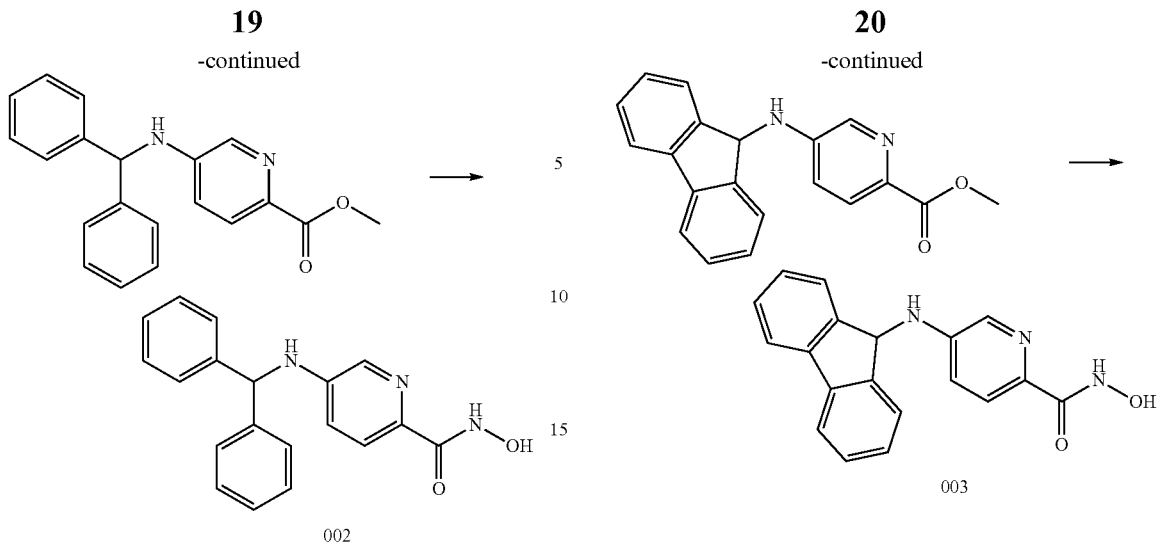

002

Step 1:

A mixture of the diphenylmethanamine (648 mg, 3 mmol), methyl 5-bromopicolinate (1.67 g, 9 mmol), Pd$_2$(dba)$_3$ (275 mg, 0.3 mmol), Xantphos (143 mg, 0.3 mmol) and Cs$_2$CO$_3$ (1.22 g, 9 mmol) in toluene (20 ml) was stirred at 95° C. overnight under N$_2$ atmosphere. The mixture was filtered and concentrated to obtain a residue, which was washed by Et$_2$O (10 ml) to afford methyl 5-(benzhydrylamino)picolinate (636 mg, 66%) as a yellow solid.

Step 2:

To a solution of methyl 5-(benzhydrylamino)picolinate (636 mg, 2 mmol) in MeOH (5 ml) was added NaOH in MeOH (5 ml), NH$_2$OH (50%) (5 ml) at 0° C., and stirred for 3 h. To the mixture was added HCl (Conc. 4 ml), EtOAc (100 ml), stirred for 30 mins, the organic layer was separated, dried and concentrated to obtain a residue, which was washed by Et$_2$O (10 ml) to afford Compound 002 (350 mg, 55%) as a yellow solid. $^1$H NMR (400 MHz, DMSO) δ 10.85 (s, 1H), 8.75 (s, 1H), 8.01 (s, 1H), 7.81-6.81 (m, 13H), 5.78 (s, 1H). LCMS: m/z=320 (M+H)$^+$.

Example 3—Synthesis of Compound 003

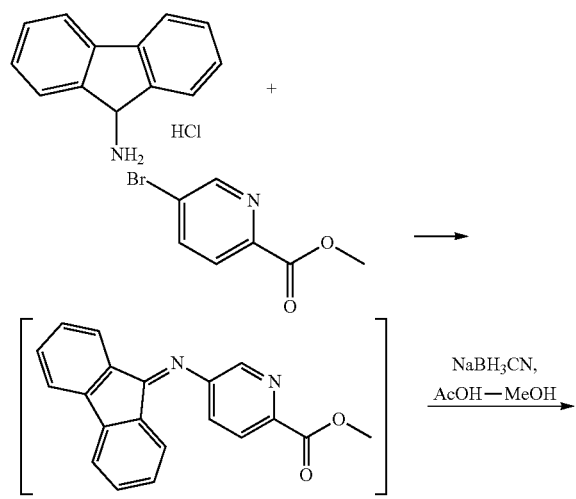

Step 1:

Under N$_2$, a mixture 9H-fluoren-9-amine hydrochloride (100 mg, 0.46 mmol) and methyl 5-bromopicolinate (105 mg, 0.49 mmol), tris(dibenzylideneacetone)dipalladium (21 mg, 0.023 mmol), RuPhos (43 mg, 0.092 mmol) and cesium carbonate (450 mg, 1.38 mmol) in toluene (4 ml) was heated at 100° C. for 18 hrs. Then it was cooled to room temperature and filtrated. The filtrate was dissolved in methanol (1 ml) and acetic acid (1 ml). Sodium cyanoborohydride (58 mg, 0.92 mmol) was added at 0° C. It was stirred at 0° C. to room temperature for 6 hrs. Then it was concentrated in vacuo. The residue was mixed with saturated aqueous sodium bicarbonate solution and extracted with EtOAc. The combined organic layers were concentrated in vacuo and the residue was purified by pre-TLC to give compound methyl 5-(9H-fluoren-9-ylamino)picolinate as an oil. (130 mg, 90%).

Step 2:

A mixture of methyl 5-(9H-fluoren-9-ylamino)picolinate (130 mg, 0.41 mmol) in DCM (2 ml) was added NH$_2$OH (2 ml), followed by NaOH solution (saturated in MeOH, 2 ml) dropwise at 0° C. The mixture was stirred at 0° C. to room temperature for 18 hrs. HCl (2 M) was added to adjust pH 7. Then it was extracted with EtOAc. The combined organic layers were concentrated in vacuo and the residue was purified by pre-HPLC to give Compound 003 as a white solid (21 mg, 16% lots SP-0017146-110). LCMS: m/z=317.9 (M+H)$^+$. $^1$H NMR (400 MHz, DMSO) δ 10.84 (s, 1H), 8.73 (s, 1H), 7.93 (d, J=7.6 Hz, 2H), 7.73 (brs, 1H), 7.64 (d, J=8.8 Hz, 1H), 7.51 (d, J=6.8 Hz, 2H), 7.44 (t, J=7.6 Hz, 2H), 7.31 (m, 3H), 7.10 (brd, J=8.4 Hz 1H), 5.82 (d, J=8.8 Hz, 1H).

Example 4—Synthesis of Compound 004

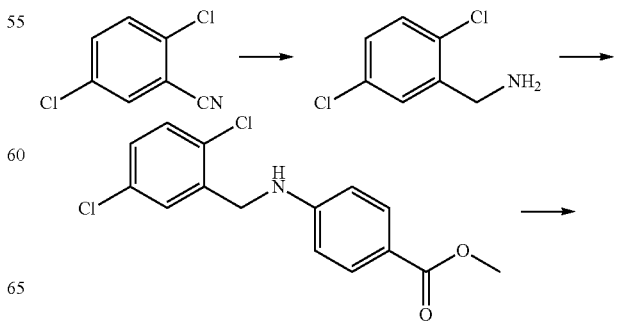

-continued

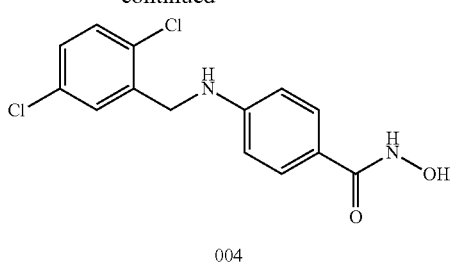

004

Step 1:

To a solution of 2,5-dichlorobenzonitrile (1.0 g, 5.8 mmol) in Dry THF was added LiAlH₄ (550 mg, 2.5 eq) in 0° C. The mixture was stirred for 2 h, after completion, the mixture was quenched with water, extracted with EtOAc (50 ml), the combined organic layers were concentrated in vacuo and to the residue, HCl-Dioxane (5 ml) was added to form the HCl salt as a white solid (840 mg, yield: 75%).

Step 2:

To a solution of (2,5-dichlorophenyl)methanamine (300 mg, 1.7 mmol) and methyl 4-iodobenzoate (445 mg, 1.7 mmol) in toluene (10 ml) was added Ruphos (10 mg), Pd₂(dba)₃ (20 mg) and Cs₂CO₃ (1.1 g, 2.0 eq). The mixture was heated at 100° C. overnight. After completion, the mixture was purified via column chromatography with PET/EtOAc=3:1 to afford the desired product as a white solid (142 mg, 31%).

Step 3:

To a solution of methyl 4-(2,5-dichlorobenzylamino)benzoate (142 mg, 0.45 mmol) in MeOH (1.5 ml) and DCM (1.5 mL) was added 50% NH₂OH (0.5 ml) and saturated NaOH in MeOH (0.5 ml) at 0° C. dropwise. Two hours later, LCMS was monitored. The mixture was acidified with 2N HCl to PH 6-7, and it was extracted by EtOAc (2×20 ml). After concentration, Compound 004 (95 mg, 68%) was obtained as a white solid. $^1$H NMR (400 MHz, DMSO) δ 10.78 (s, 1H), 8.70 (s, 1H), 7.60-7.46 (m, 2H), 7.41-7.32 (m, 2H), 6.83 (s, 1H), 6.55 (d, J=8.7 Hz, 2H), 4.37 (d, J=6.0 Hz, 2H). LCMS: m/z=312 (M+H)$^+$.

Example 5—Synthesis of Compound 005

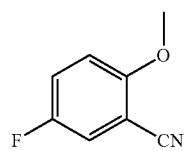

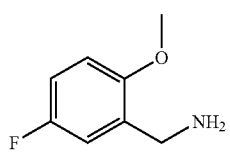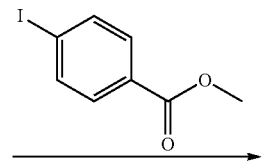

-continued

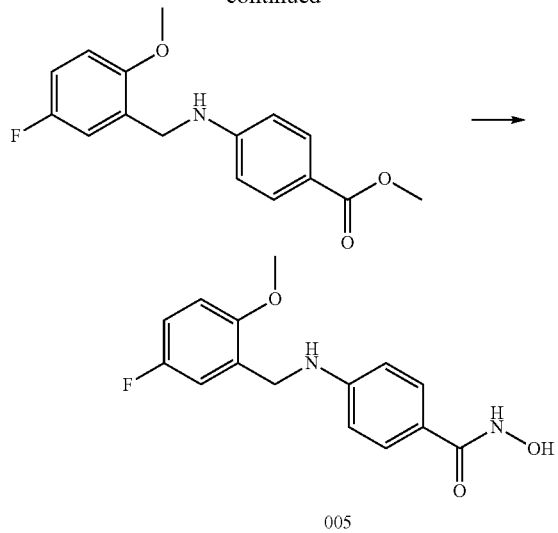

005

Step 1:

To a solution of 5-fluoro-2-methoxybenzonitrile (4.2 g, 27.8 mmol) in dry THF (25 ml) was added LiAlH₄ (2.6 g, 2.5 eq) in 0° C. The mixture was stirred for 2 h, after completion, the mixture was quenched with water, extracted with EtOAc (150 ml), the combined organic layers were concentrated in vacuo to afford the crude product as a yellow oil (4.2 g).

Step 2:

To a solution of (5-fluoro-2-methoxyphenyl)methanamine (200 mg, crude) and methyl 4-iodobenzoate (342 mg, 1.3 mmol) in toluene (10 ml) was added Ruphos (10 mg), Pd₂(dba)₃ (20 mg) and Cs₂CO₃ (846 mg, 2.0 eq). The mixture was heated at 100° C. overnight. After completion, the mixture was purified on column with PET/EtOAc=3:1 to afford the desired product as a yellow solid (200 mg).

Step 3:

To a solution of methyl 4-(2,5-dichlorobenzylamino)benzoate (200 mg, crude) in MeOH (1.5 ml) and DCM (1.5 mL) was added 50% NH₂OH (0.5 ml) and saturated NaOH in MeOH (0.5 ml) at 0° C. dropwise. Two hours later, LCMS was monitored. The mixture was acidified with 2N HCl to PH 6-7. It was extracted by EtOAc (2×20 ml). After concentrated and purification on prep-HPLC, Compound 005 (75 mg) was obtained as a white solid. $^1$H NMR (400 MHz, DMSO) δ 10.75 (s, 1H), 8.67 (s, 1H), 7.50 (d, J=7.3 Hz, 2H), 7.00 (dd, J=21.9, 9.3 Hz, 3H), 6.66 (s, 1H), 6.52 (d, J=7.4 Hz, 2H), 4.25 (d, J=5.0 Hz, 2H), 3.83 (s, 3H). LCMS: m/z=291 (M+H)$^+$.

Example 6—Synthesis of Compound 006

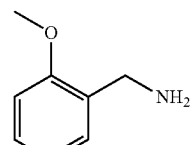

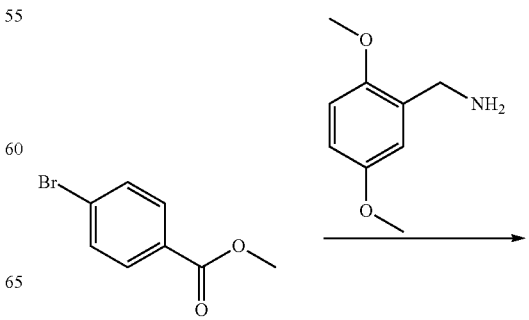

-continued

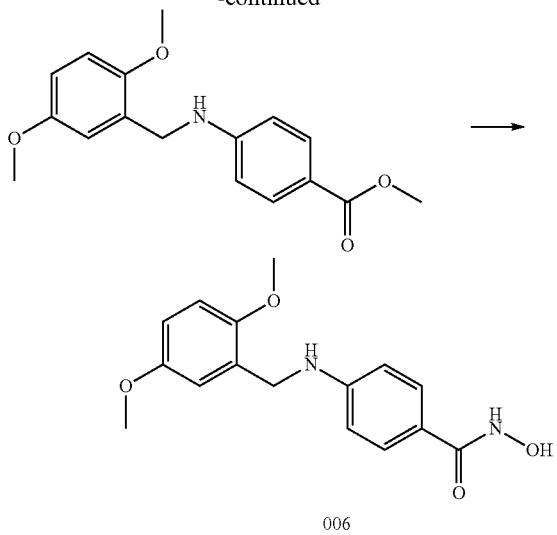

006

Step 1:
A mixture of the methyl 4-bromobenzoate (430 mg, 2 mmol), (2,5-dimethoxyphenyl)-methanamine (668 mg, 4 mmol), Pd$_2$(dba)$_3$ (183 mg, 0.2 mmol), RuPhos (96 mg, 0.2 mmol) and Cs$_2$CO$_3$ (1.95 g, 6 mmol) in toluene (15 mL) was stirred at 95° C. under N$_2$ atmosphere overnight. To the mixture was added EtOAc (100 mL), filtered and concentrated to obtain a residue, which was washed by PET to obtain methyl 4-(2,5-dimethoxybenzylamino)benzoate (481 mg, 80%) as a yellow solid.

Step 2:
To a solution of methyl 4-(2,5-dimethoxybenzylamino) benzoate (300 mg, 1 mmol) in MeOH (5 mL) was added NaOH in MeOH (5 mL), NH$_2$OH (50%, 5 mL) at 0° C., and stirred for 3 h. To the mixture was added HCl (Conc. 4 ml), EA (100 ml), stirred for 30 mins, the organic layer was separated, dried and concentrated to obtain a residue, which was purified by Prep-HPLC to obtain Compound 006 (227 mg, 75%) as a yellow solid. LCMS: m/z=303 (M+H)$^+$ $^1$H NMR (400 MHz, DMSO) δ 7.50 (d, J=8.7 Hz, 2H), 6.92 (d, J=8.5 Hz, 1H), 6.79 (d, J=3.0 Hz, 2H), 6.53 (d, J=8.8 Hz, 2H), 4.23 (s, 2H), 3.78 (s, 3H), 3.63 (s, 3H).

Example 7—Synthesis of Compound 011

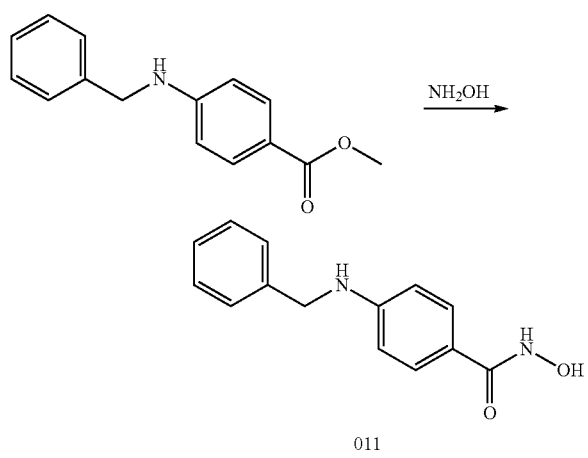

011

To a solution of methyl 4-(benzylamino)benzoate (100 mg, 0.41 mmol) in MeOH (1.5 ml) and DCM (1.5 mL) was added 50% NH$_2$OH (0.5 ml) and saturated NaOH in MeOH (0.5 ml) at 0° C. dropwise. Two hours later, LCMS was monitored. The mixture was acidified with 2N HCl to PH 6-7. It was extracted by EtOAc (2×10 ml). After concentrated and purification on prep-TLC (DCM/MeOH=20:1), Compound 011 (40 mg, 40%) was obtained as a white solid. $^1$H NMR (400 MHz, DMSO) δ 10.74 (s, 1H), 8.67 (s, 1H), 7.50 (d, J=7.3 Hz, 2H), 7.35-7.32 (m, 5H), 7.24 (m, 1H), 7.22 (d, J=7.4 Hz, 2H), 4.31-4.30 (d, J=5.0 Hz, 2H). LCMS: m/z=243 (M+H)$^+$.

Example 8—Synthesis of Compound 012

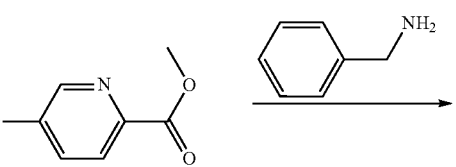

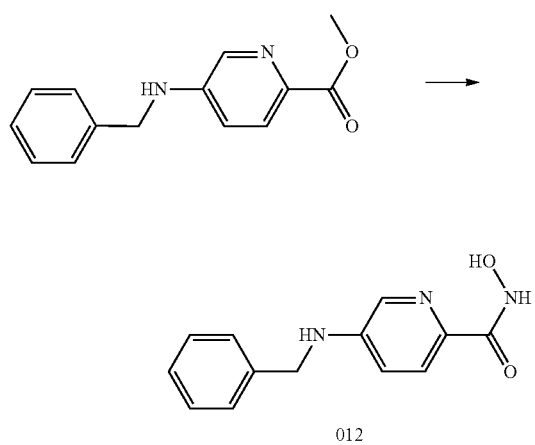

012

Step 1:
To a solution of methyl 5-bromopicolinate (186 mg, 1.74 mmol) and phenylmethanamine (250 mg, 1.16 mmol), K$_2$CO$_3$ (240 mg, 1.74 mmol), Ruphos (5.4 mg, 0.01 mmol), Pd$_2$dba$_3$ (10.6 mg, 0.01 mmol) in toluene (5 ml) was stirred at 95° C. under N2 protection for overnight. The solution was evaporated off and extracted by EtOAc (10 ml×2), washed with water, brine, purified by prep-TLC (PET/EtOAc=1/1) to afford a yellow liquid (74 mg, 30.8%).

Step 2:
To a solution of methyl 5-(benzylamino)picolinate (150 mg, 0.61 mmol) NH2OH (4 ml, 1.76 mmol), NaOH(Sat. in CH3OH, 2 ml, 0.88 mmol) in DCM (1 ml) and MeOH (2 ml) was stirred at 0° C. for 2 h. The solvent was evaporated off, adjust to pH 7-8, filtered and washed with water to afford Compound 012 as a white solid (64 mg, 42.6%). $^1$H NMR (400 MHz, DMSO) δ 10.83 (s, 1H), 8.74 (s, 1H), 7.92 (d, J=2.7 Hz, 1H), 7.66 (d, J=8.6 Hz, 1H), 7.38-7.30 (m, 4H), 7.25 (dd, J=10.8, 4.2 Hz, 1H), 7.09 (t, J=5.9 Hz, 1H), 6.96 (dd, J=8.6, 2.8 Hz, 1H), 4.36 (d, J=6.0 Hz, 2H). LCMS: m/z=244 (M+H)$^+$.

Example 9—Synthesis of Compound 013

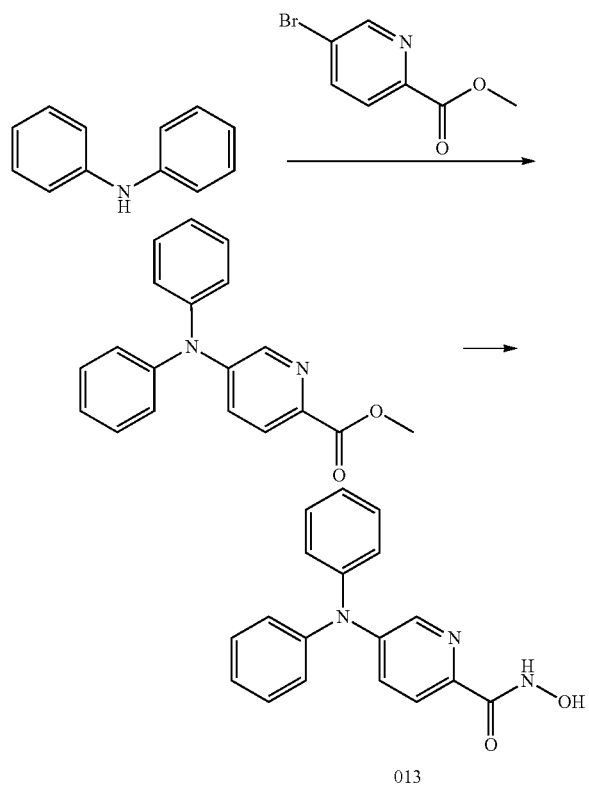

Step 1:
To a solution of methyl 5-bromopicolinate (200 mg, 0.9 mmol) in toluene (6 ml) was added diphenylamine (470 mg, 3.0 eq.), Ruphos (43 mg, 0.1 eq.), Pd$_2$(dba)$_3$ (85 mg, 0.1 eq.), Cs$_2$CO$_3$ (905 mg, 3.0 eq.) at 95° C. o/n under N$_2$ atmosphere. It was filtered through celita. It was extracted with EtOAc (2×70 ml) and washed by brine (2×50 ml). It was purified by pre-TLC (PET:EtOAc=2:1). A Pale yellow solid methyl 5-(diphenylamino)picolinate (130 mg, 46%) was obtained.

Step 2:
To a solution of methyl 5-(diphenylamino)picolinate (130 mg, 0.43 mmol) in MeOH (1 ml) and DCM (1 ml) was added 50% NH$_2$OH (0.5 ml) and saturated NaOH in MeOH (0.5 ml) at 0° C. dropwise. Two hours later, LCMS was monitored. The mixture was acidified with 2N HCl to PH 6-7. It was extracted by EtOAc (2×60 ml). After concentrated, Compound 013 (88 mg, 67%) was obtained as a pale yellow solid. 1H NMR (400 MHz, DMSO) δ 11.14 (s, 1H), 8.96 (s, 1H), 8.05 (s, 1H), 7.83 (d, J=8.5 Hz, 1H), 7.47-7.29 (m, 5H), 7.18 (dd, J=19.0, 7.5 Hz, 6H). LCMS: m/z=306 (M+H)$^+$.

Example 10—Synthesis of Compound 014

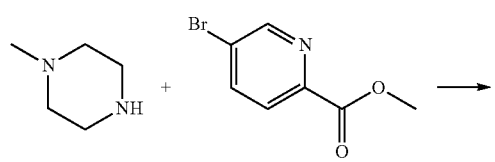

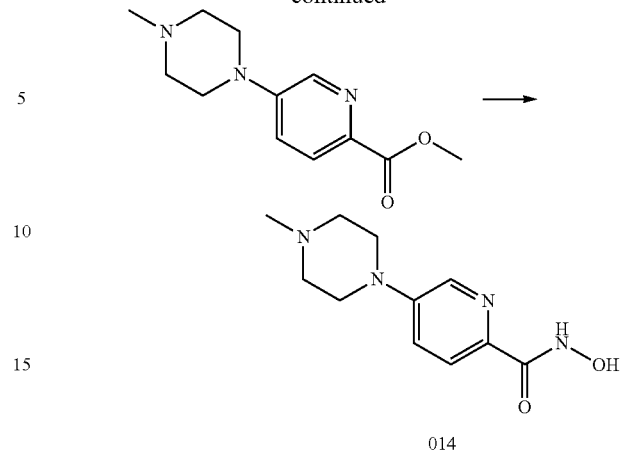

Step 1:
Under N$_2$, a mixture 1-methylpiperazine (440 mg, 4.44 mmol) and methyl 5-bromopicolinate (800 mg, 3.70 mmol), tris(dibenzylideneacetone)dipalladium (170 mg, 0.19 mmol), S-Phos (304 mg, 0.74 mmol) and potassium phosphate (1.10 g, 5.18 mmol) in toluene (20 ml) was heated at 100° C. for 3 days. Then it was cooled to room temperature and filtrated. The filtrate was concentrated in vacuo, and the residue was purified by silica gel chromatography (PET/EtOAc=1:1, EtOAc) to give desired product as a white solid (200 mg, 23%).

Step 2:
A mixture of methyl 5-(4-methylpiperazin-1-yl)picolinate (200 mg, 0.85 mmol) in DCM (2 ml) was added NH$_2$OH (50% in water, 2 ml), followed by NaOH solution (saturated in MeOH, 2 ml) dropwise at 0° C. The mixture was stirred at 0° C. to room temperature for 18 hrs. HCl (2 M) was added to adjust pH 7. Then it was extracted with EtOAc. The combined organic layers were concentrated in vacuo and the residue was purified by pre-HPLC to give Compound 014 as a grey solid (29 mg, 10% lots SP-0017146-078). LCMS: m/z=237.2 (M+H)$^+$. $^1$H NMR (400 MHz, DMSO) δ 11.02 (brs, 1H), 8.85 (brs, 1H), 8.24 (d, J=2.8 Hz, 1H), 7.78 (d, J=8.8 Hz, 1H), 7.39 (dd, J=8.8, 2.8 Hz, 1H), 3.30 (m, 4H), 2.45 (m, 4H), 2.22 (s, 3H).

Example 11—Synthesis of Compound 015

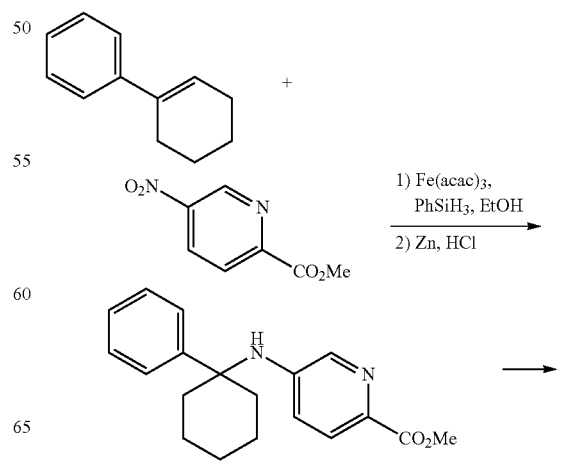

-continued

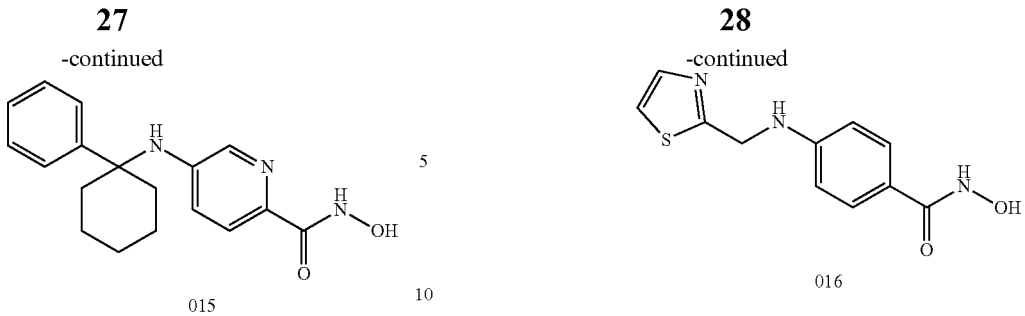

015

Step 1:

To a solution of methyl 5-nitropicolinate (500 mg, 2.75 mmol) and Fe(acac)₃ (291 mg, 0.82 mmol) in methanol (28 mL) was added cyclohexenylbenzene (1.30 g, 8.24 mmol) and phenylsilane (683 μL, 5.49 mmol). It was heated at 60° C. for 1 hr. Then zinc (3.59 g, 54.9 mmol) and aqueous HCl solution (0.3 M) were added. The mixture was heated at 60° C. for 1 hr. Then it was cooled to r.t. and filtrated. The filtrate was neutralized with saturated aqueous sodium bicarbonate solution and extracted with EA. The combined EA layers were concentrated in vacuo and the residue was purified by silica gel chromatography to give compound methyl 5-(1-phenylcyclohexylamino)picolinate as a light yellow solid (190 mg, yield: 22%).

Step 2:

To a mixture of methyl 5-(1-phenylcyclohexylamino) picolinate (190 mg, 0.61 mmol) in DCM (2 ml) was added NH₂OH (50% in water, 2 ml), followed by NaOH solution (saturated in MeOH, 2 ml) dropwise at 0° C. The mixture was stirred at 0° C. to room temperature for 18 hrs. HCl (2 M) was added to adjust pH 7. Then it was extracted with EtOAc. The combined organic layers were concentrated in vacuo and the residue was purified by pre-HPLC to give Compound 015 as a white solid (104 mg, yield: 54% lots SP-0017146-118). LCMS: m/z=312.0 (M+H)⁺. ¹H NMR (400 MHz, DMSO) δ 10.80 (s, 1H), 8.77 (brs, 1H), 7.77 (d, J=2.8 Hz, 1H), 7.45 (m, 3H), 7.33 (t, J=8.0 Hz, 2H), 7.21 (m, 1H), 6.67-6.64 (m, 2H), 2.12 (m, 2H), 1.79 (m, 2H), 1.67 (m, 3H), 1.55 (m, 2H), 1.29 (m, 1H).

Example 12—Synthesis of Compound 016

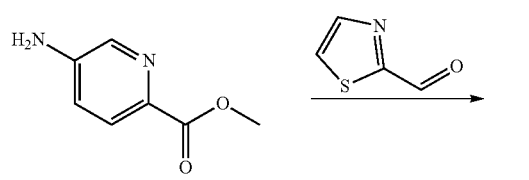

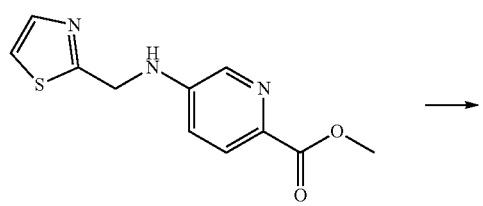

-continued

016

Step 1:

A mixture of the methyl 5-aminopicolinate (456 mg, 3 mmol), thiazole-2-carbaldehyde (339 mg, 3 mmol) and NaBH₃CN (189 mg, 3 mmol) in MeOH (10 ml) was stirred at 60° C. under N₂ atmosphere for 3 h. The mixture was concentrated to get a residue, which was washed by Prep-TLC to afford methyl 5-(thiazol-2-ylmethylamino)picolinate (261 mg, 35%) as a yellow solid.

Step 2:

A solution of methyl 5-(thiazol-2-ylmethylamino)picolinate (150 mg, 0.6 mmol) in MeOH (5 ml) was added NaOH in MeOH (5 ml), NH₂OH (50%) (5 ml) at 0° C., and stirred for 3 h. The mixture was was purified by Prep-HPLC to afford Compound 016 (45 mg, 30%) as a yellow solid. LCMS: m/z=251 (M+H)⁺, ¹H NMR (400 MHz, DMSO) δ 10.93 (s, 1H), 8.83 (s, 1H), 7.97 (d, J=2.5 Hz, 1H), 7.77 (d, J=3.2 Hz, 1H), 7.70 (d, J=8.6 Hz, 1H), 7.63 (d, J=3.2 Hz, 1H), 7.39 (t, J=5.9 Hz, 1H), 7.03 (dd, J=8.6, 2.6 Hz, 1H), 4.71 (d, J=6.1 Hz, 2H).

Example 13—Synthesis of Compound 017

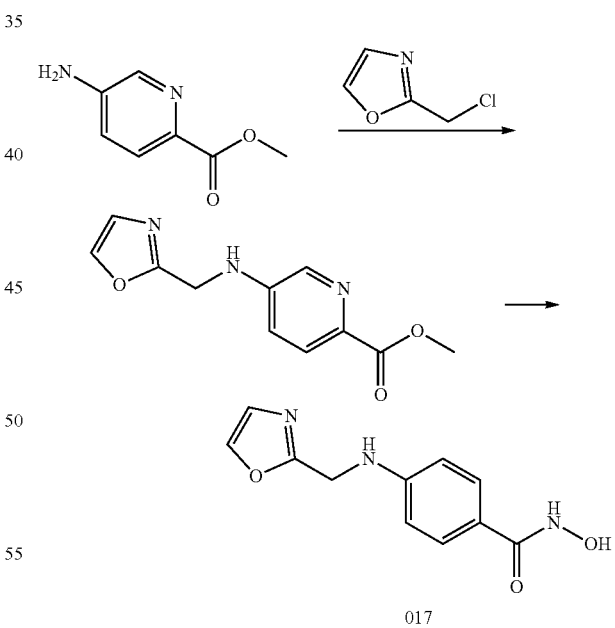

017

Step 1:

A mixture of the methyl 5-aminopicolinate (456 mg, 3 mmol), 2-(chloromethyl)oxazole (354 mg, 3 mmol) in H₂O (10 ml) was stirred at 80° C. under N₂ atmosphere for overnight. The mixture was concentrated to get a residue, which was washed by Prep-TLC to afford methyl 5-(oxazol-2-ylmethylamino)picolinate (140 mg, 20%) as a yellow solid.

Step 2:

A solution of methyl 5-(oxazol-2-ylmethylamino)picolinate (140 mg, 0.6 mmol) in MeOH (5 ml) was added NaOH in MeOH (5 ml), NH$_2$OH (50%, 5 ml) at 0° C., and stirred for 3 h. The mixture was purified by Pre-HPLC to afford Compound 017 (56 mg, 40%) as a yellow solid. LCMS: m/z=235 (M+H)$^+$, $^1$H NMR (400 MHz, DMSO) δ 10.91 (s, 1H), 8.38 (s, 1H), 8.03 (m, 2H), 7.68 (s, 1H), 7.25-6.92 (m, 3H), 4.52 (d, J=5.7 Hz, 2H).

Example 14—Synthesis of Compound 018

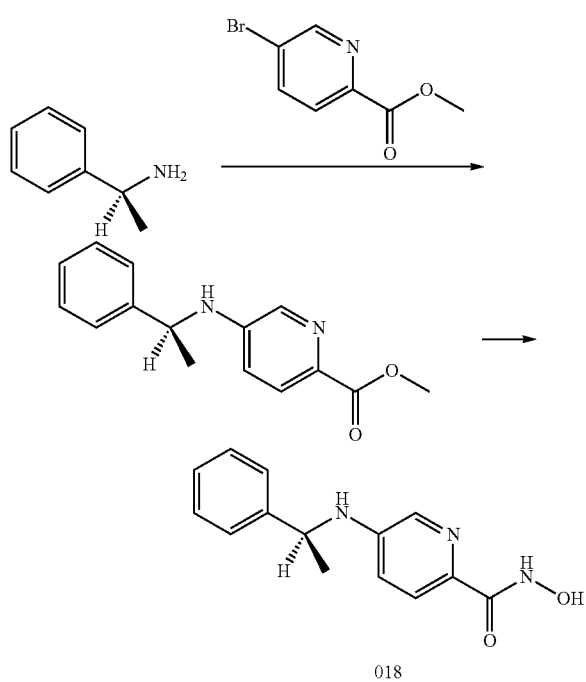

018

Step 1:

To a solution of methyl 5-bromopicolinate (214 mg, 1.0 mmol) in toluene (5 ml) was added (S)-1-phenylethanamine (145 mg, 1.2 eq.), Ruphos (46 mg, 0.1 eq.), Pd$_2$(dba)$_3$ (115 mg, 0.1 eq.), Cs$_2$CO$_3$ (650 mg, 2.0 eq.) at 95° C. overnight under N$_2$ atmosphere. It was filtered through celite. It was extracted with EtOAc (2×50 ml) and washed by brine (2×50 ml). After dried by Na$_2$SO$_4$, it was concentrated and washed with Et$_2$O. A Pale yellow solid (S)-methyl 5-(1-phenylethylamino)picolinate (175 mg, 68%) was obtained.

Step 2:

To a solution of (S)-methyl 5-(1-phenylethylamino)picolinate (175 mg, 0.63 mmol) in MeOH (2 ml) and DCM (2 mL) was added 50% NH$_2$OH (1 ml) and saturated NaOH in MeOH (1 ml) at 0° C. dropwise. Two hours later, LCMS was monitored. The mixture was acidified with 2N HCl to PH 6-7. It was extracted by EtOAc (2×60 ml). After concentration, Compound 018 (57 mg, 34%) was obtained as a yellow solid. 1H NMR (400 MHz, DMSO) δ 7.85 (d, J=2.5 Hz, 1H), 7.58 (d, J=8.6 Hz, 1H), 7.37 (d, J=7.2 Hz, 2H), 7.31 (t, J=7.6 Hz, 2H), 7.20 (t, J=7.2 Hz, 1H), 7.02 (d, J=6.8 Hz, 1H), 6.84 (dd, J=8.6, 2.6 Hz, 1H), 4.58 (t, J=6.8 Hz, 1H), 1.45 (d, J=6.7 Hz, 3H). LCMS: m/z=258 (M+H)$^+$.

Example 15—Synthesis of Compound 019

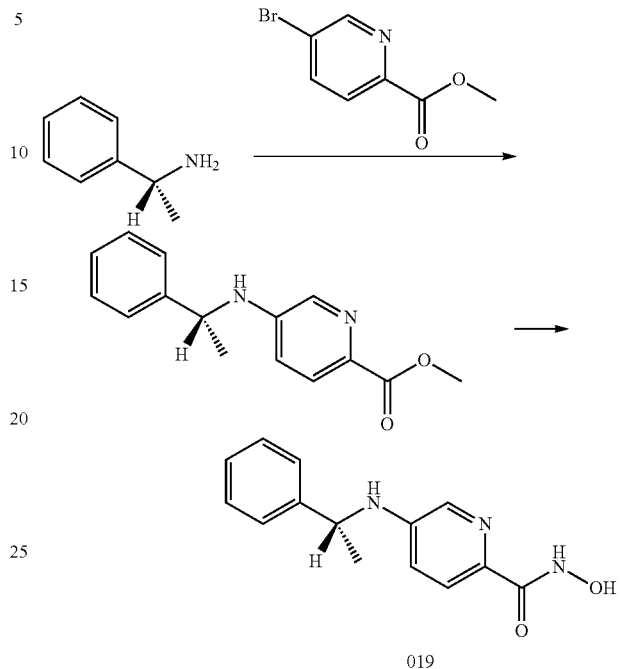

019

Step 1:

To a solution of methyl 5-bromopicolinate (200 mg, 0.93 mmol) in toluene (6 ml) was added (R)-1-phenylethanamine (336 mg, 3.0 eq.), Ruphos (43 mg, 0.1 eq.), Pd$_2$(dba)$_3$ (85 mg, 0.1 eq.), Cs$_2$CO$_3$ (905 mg, 3.0 eq.) at 95° C. overnight under N$_2$ atmosphere. It was filtered through celite. It was extracted with EtOAc (2×70 ml) and washed by brine (2×50 ml). After dried by Na$_2$SO$_4$, it was concentrated and washed with Et$_2$O. A Pale yellow solid (R)-methyl 5-(1-phenylethylamino)picolinate (181 mg, 76%) was obtained.

Step 2:

To a solution of (R)-methyl 5-(1-phenylethylamino)picolinate (161 mg, 0.63 mmol) in MeOH (1.5 ml) and DCM (1.5 mL) was added 50% NH$_2$OH (0.5 ml) and sat. NaOH in MeOH (0.5 ml) at 0° C. dropwise. Two hours later, LCMS was monitored. The mixture was acidified with 2N HCl to PH 6-7. It was extracted by EtOAc (2×60 ml). After concentration, Compound 019 (39 mg, 24%) was obtained as a white solid. 1H NMR (400 MHz, DMSO) δ 10.79 (s, 1H), 8.72 (s, 1H), 7.85 (d, J=2.6 Hz, 1H), 7.59 (d, J=8.6 Hz, 1H), 7.37 (d, J=7.1 Hz, 2H), 7.31 (t, J=7.6 Hz, 2H), 7.20 (t, J=7.2 Hz, 1H), 7.04 (d, J=6.9 Hz, 1H), 6.85 (dd, J=8.7, 2.7 Hz, 1H), 4.58 (t, J=6.8 Hz, 1H), 1.45 (d, J=6.7 Hz, 3H). LCMS: m/z=258 (M+H)$^+$.

Example 16—Synthesis of Compound 020

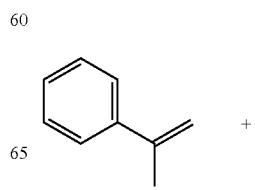

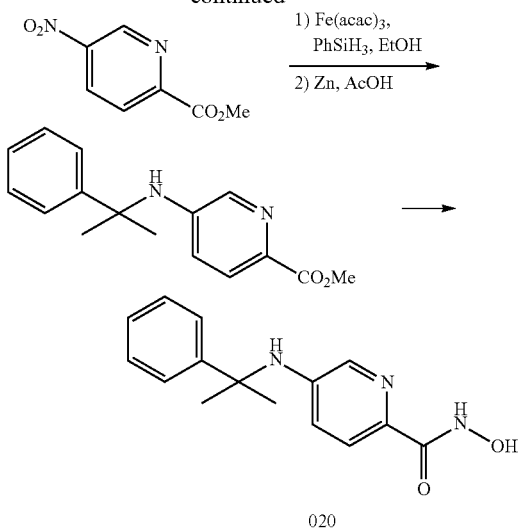

Step 1:

To a methyl 5-nitropicolinate (200 mg, 1.1 mmol) and Fe(acac)₃ (116 mg, 0.33 mmol) in methanol (10 mL) was added prop-1-en-2-ylbenzene (389 g, 3.3 mmol) and phenylsilane (785, 3.3 mmol). It was heated at 60° C. for 1 hr. Then zinc (3.59 g, 54.9 mmol) and AcOH (10 mL) were added. The mixture was heated at 60° C. for 1 hr. Then it was cooled to room temperature and filtrated. The filtrate was neutralized with saturated aqueous sodium bicarbonate solution and extracted with EtOAc. The combined organic layers were concentrated in vacuo and the residue was purified by silica gel chromatography to give methyl 5-(2-phenylpropan-2-ylamino)picolinate as a light yellow solid (140 mg, yield: 47%).

Step 2:

A mixture of methyl 5-(2-phenylpropan-2-ylamino)picolinate (140 mg, 0.52 mmol) in DCM (2 ml) was added NH₂OH (50% in water, 2 ml), followed by NaOH solution (sat. in MeOH, 2 ml) dropwise at 0° C. The mixture was stirred at 0° C. to room temperature for 18 hrs. HCl (2 M) was added to adjust pH 7. Then it was extracted with EtOAc. The combined organic layers were concentrated in vacuo and the residue was purified by pre-HPLC to give Compound 020 as a white solid (70 mg, yield: 43% lots SP-0017456-102). LCMS: m/z=272 (M+H)⁺. ¹H NMR (400 MHz, DMSO) δ 10.79 (s, 1H), 8.74 (s, 1H), 7.66 (d, J=2.6 Hz, 1H), 7.49 (d, J=8.7 Hz, 1H), 7.42 (d, J=7.4 Hz, 2H), 7.34 (t, J=7.7 Hz, 2H), 7.23 (t, J=7.2 Hz, 1H), 6.90 (s, 1H), 6.58 (dd, J=8.7, 2.7 Hz, 1H), 1.60 (s, 6H).

Example 17—HDAC Enzyme Assays

Compounds for testing were diluted in DMSO to 50 fold the final concentration and a ten-point three-fold dilution series was made. The compounds were diluted in assay buffer (50 mM HEPES, pH 7.4, 100 mM KCl, 0.001% Tween-20, 0.05% BSA, 20 πM TCEP) to 6-fold their final concentration. The HDAC enzymes (purchased from BPS Biosciences) were diluted to 1.5-fold their final concentration in assay buffer. The tripeptide substrate and trypsin at 0.05 μM final concentration were diluted in assay buffer at 6-fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 μM (HDAC1), 10 μM (HDAC2), 17 μM (HDAC3) and 14 μM (HDAC6).

Five μL of compounds and 20 μL of enzyme were added to wells of a black, opaque 384 well plate in duplicate. Enzyme and compound were incubated together at room temperature for 10 minutes. Five μL of substrate was added to each well, the plate was shaken for 60 seconds and placed into a Victor 2 microtiter plate reader. The development of fluorescence was monitored for 60 min and the linear rate of the reaction was calculated. The IC₅₀ was determined using Graph Pad Prism by a four parameter curve fit. The IC₅₀ values (nM) obtained for several of the compounds of this invention are found in Table 2, below.

TABLE 2

| Cmpd ID | Structure | HDAC1 | HDAC2 | HDAC3 | HDAC6 |
|---|---|---|---|---|---|
| 001 | 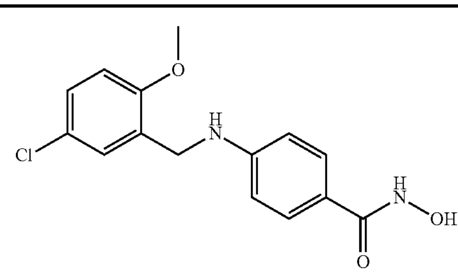 | 200-400 | 200-400 | 200-400 | 1-6 |
| 004 | 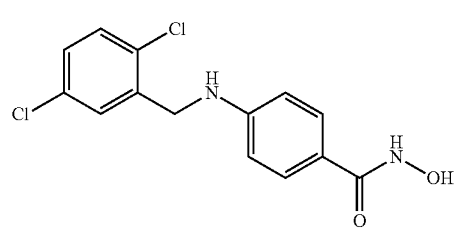 [SMILES: O=C(NO)c1ccc(NCc2cc(Cl)ccc2Cl)cc1] | 100-200 | 100-200 | 100-200 | 4-8 |

TABLE 2-continued

| Cmpd ID | Structure | HDAC1 | HDAC2 | HDAC3 | HDAC6 |
|---|---|---|---|---|---|
| 005 | 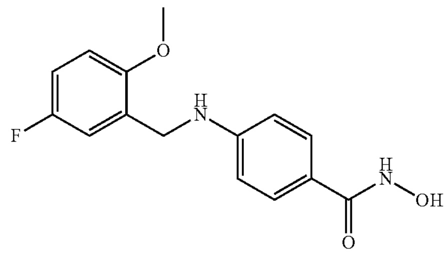 [SMILES: COc1ccc(F)cc1CNc1ccc(C(=O)NO)cc1] | 500-800 | 500-800 | 500-800 | 1-6 |
| 006 | 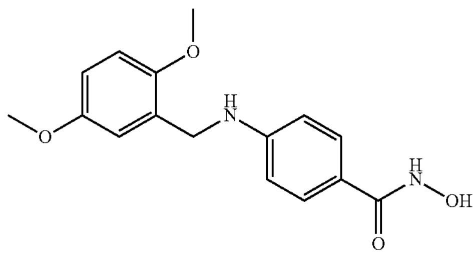 [SMILES: COc1ccc(OC)c(CNc2ccc(C(=O)NO)cc2)c1] | 450-600 | 900-1100 | 900-1100 | 30-40 |
| 007 | 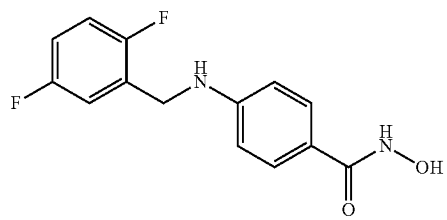 [SMILES: O=C(NO)c1ccc(NCc2cc(F)ccc2F)cc1] | 450-600 | 450-600 | 700-800 | 4-8 |
| 008 | 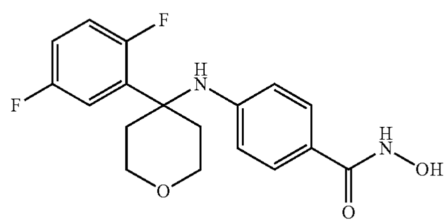 [SMILES: O=C(NO)c1ccc(NC2(c3cc(F)ccc3F)CCOCC2)cc1] | 150-250 | 200-300 | 1000-1100 | 0.1-1 |
| 009 | 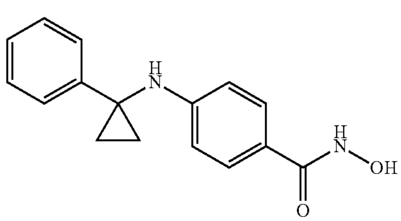 [SMILES: O=C(NO)c1ccc(NC2(c3ccccc3)CC2)cc1] | 50-100 | 250-350 | 400-500 | 0.5-2.5 |
| 010 | 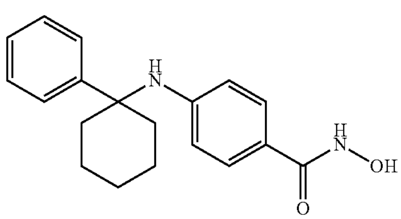 [SMILES: O=C(NO)c1ccc(NC2(c3ccccc3)CCCCC2)cc1] | 1000-2000 | 1500-2000 | 6000-7000 | 4-8 |

TABLE 2-continued

| Cmpd ID | Structure | HDAC1 | HDAC2 | HDAC3 | HDAC6 |
|---|---|---|---|---|---|
| 011 | 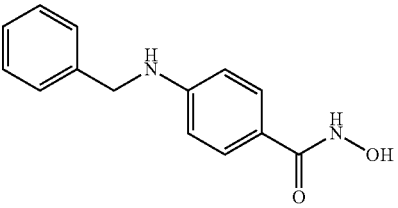 [SMILES: O=C(NO)c1ccc(NCc2ccccc2)cc1] | 700-800 | 800-900 | 1200-1300 | 15-25 |

Example 18—Rat Pharmacokinetic Studies

Male SD rats were fasted overnight. Compounds of the invention were dissolved in dimethyl acetamide at 10 times the final concentration, then Solutol HS 15 (BASF) was added to a final concentration of 10%. Finally 80% saline was added and vortexed to achieve a clear solution. For the IV dosing three animals were injected via the foot dorsal vein with 1 mg/kg compound. For the PO dosing 5 mg/kg of compound was delivered by oral gavage. Blood was collected via the tail vein into K2EDTA tubes at 5 minutes, 15 minutes, 30 minutes, 1 hour, 2 hours, 4 hours, 8 hours and 24 hours after dosing. The blood was centrifuged at 2000 g for 5 minutes at 4° C. to obtain plasma. The plasma was extracted with acetonitrile and the level of compound was analyzed by LC/MS/MS. The level of compound in plasma was calculated from a standard curve in rat plasma. The IV clearance and area under the curve were calculated using WinNonLin software. The dose adjusted area under the curve for the IV and oral dosing were used to calculate the oral bioavailability. A summary of results is presented in Table 3.

TABLE 3

| Compound | Rat IV Clearance (L/hr/kg) |
|---|---|
| Compound 001 | 1-5 |
| Compound 005 | 10-20 |
| Compound 008 | 5-10 |
| Compound 009 | 3-7 |
| Compound 010 | 2-4 |
| Compound 011 | 5.5-7 |

Example 19—Mouse Pharmacokinetic Studies

Male C57BL/6 mice were fasted overnight. Compounds were dissolved in dimethyl acetamide at 10 times the final concentration, then Solutol HS 15 (BASF) was added to a final concentration of 10%. Finally 80% saline was added and vortexed to achieve a clear solution. Fifteen animals were injected intraperitonealy with 5 mg/kg compound. Blood was collected by retro-orbital bleed at 5 minutes, 15 minutes, 30 minutes, 1 hour, 2 hours, 4 hours, 8 hours and 24 hours after dosing. At 5 minutes, 30 minutes, 1 hour and 4 hours after dosing three animals per time point were sacrificed and brains were removed. The blood was centrifuged at 2000 g for 5 minutes at 4° C. to obtain plasma. Brain samples were homogenized in PBS. The plasma and brain homogenate were extracted with acetonitrile and the level of compound was analyzed by LC/MS/MS. The level of compound in plasma was calculated from a standard curve in rat plasma and the level in brain was calculated from a standard curve in brain homogenate. The area under the curve in plasma and brain were calculated using WinNonLin software. The brain to plasma ratio was determined using the area under the curve values for the two compartments. A summary of results is presented in Table 4.

TABLE 4

| Compound | Plasma AUC (hr*ng/ml) | Brain AUC (hr*ng/ml) | Brain/plasma ratio |
|---|---|---|---|
| Compound 002 | 200-250 | 450-600 | 1-5 |
| Compound 012 | 75-125 | 100-150 | 1-3 |
| Compound 013 | 150-250 | 600-800 | 2-6 |

Inhibition of HDAC1, 2 and 3 have been associated with toxicity, such as thrombocytopenia, neutropenia, anemia, and fatigue. A compound with a higher selectivity for HDAC6 over HDACs 1, 2 and 3 would therefore be expected to have a larger therapeutic window.

The invention claimed is:

1. A method of treating a neurodegenerative disorder in a subject in need thereof by inhibiting the activity of HDAC6, comprising administering to the subject a therapeutically effective amount of a compound of Formula I:

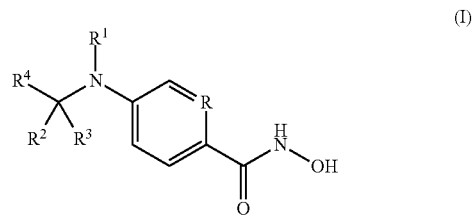

(I)

or a pharmaceutically acceptable salt thereof;
wherein
R is N;
$R^1$ is H or $C_1$-$C_3$ alkyl;
$R^2$ and $R^3$ are H; or
$R^2$ is H and $R^3$ is phenyl, wherein the phenyl ring is optionally and independently substituted with 1, 2, or 3 halo, $C_1$-$C_6$ alkyl or $C_1$-$C_6$ alkoxy groups; or
$R^2$ and $R^3$ are taken together to form a $C_3$-$C_6$ cycloalkyl ring or a $C_2$-$C_5$ heterocycloalkyl ring;
$R^4$ is phenyl, wherein the phenyl ring is optionally and independently substituted with 1, 2, or 3 halo, $C_1$-$C_6$ alkyl or $C_1$-$C_6$ alkoxy groups; and
wherein the neurodegenerative disorder is Alzheimer's disease, Huntington's disease, frontotemporal dementia, progressive supranuclear palsy, cortcobasal dementia, Parkinson's with Lewy-Body dementia, post-traumatic neurodegeneration, or chronic traumatic encephalopathy.

2. The method of claim 1, wherein the neurodegenerative disorder is Alzheimer's disease.

3. The method of claim 1, wherein $R^1$ is H.

4. The method of claim 1, wherein $R^2$ is H and $R^3$ is phenyl, wherein the phenyl ring is optionally and independently substituted with 1, 2, or 3 halo, $C_1$-$C_6$ alkyl or $C_1$-$C_6$ alkoxy groups; and $R^4$ is phenyl, wherein the phenyl ring is optionally and independently substituted with 1, 2, or 3 halo, $C_1$-$C_6$ alkyl or $C_1$-$C_6$ alkoxy groups.

5. The method of claim 4, wherein the compound of Formula I is:

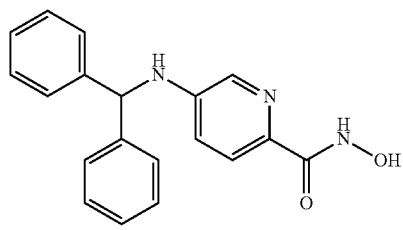 [SMILES: O=C(NO)c1ccc(NC(c2ccccc2)c2ccccc2)cn1]

or a pharmaceutically acceptable salt thereof.

6. A method of treating a neurodegenerative disorder in a subject in need thereof by inhibiting the activity of HDAC6, comprising administering to the subject a therapeutically effective amount of a compound selected from the group consisting of:

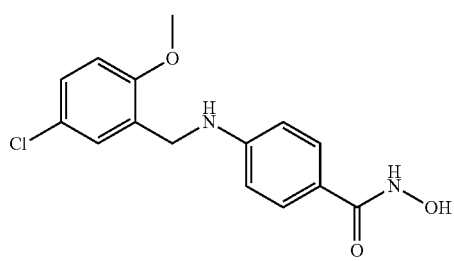

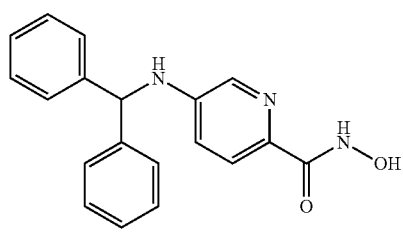

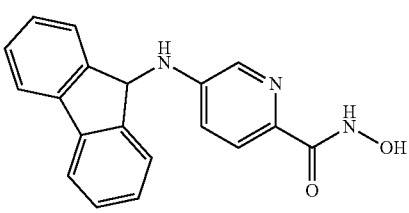

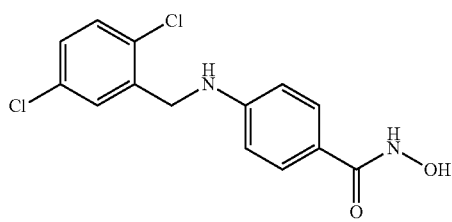

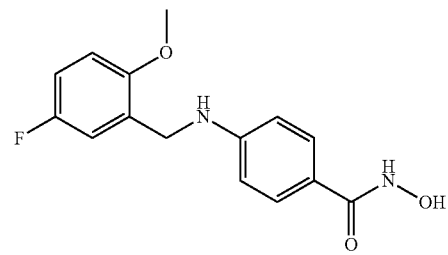

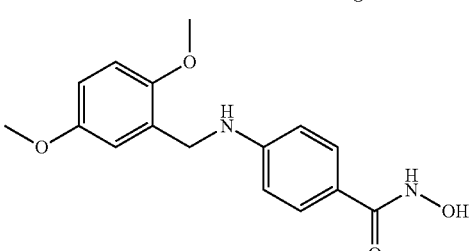

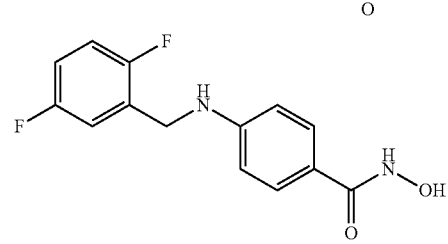

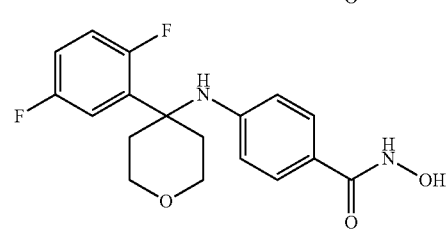

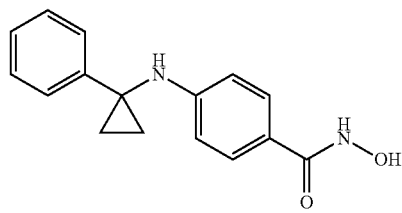

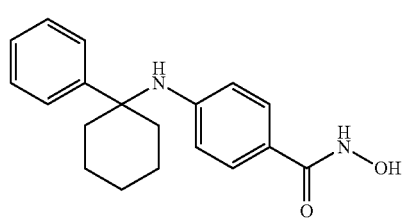

-continued

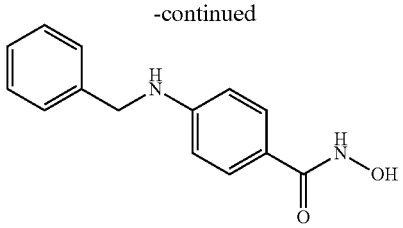

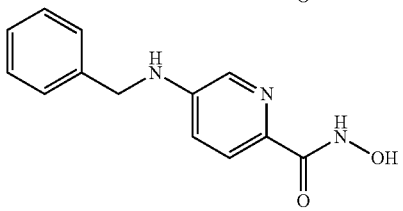

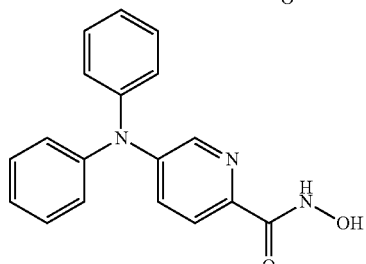

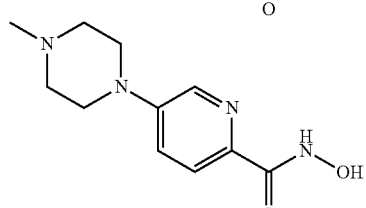

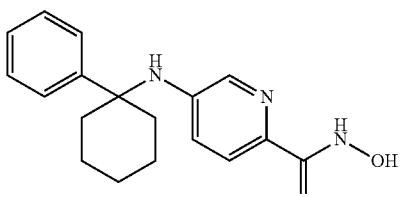

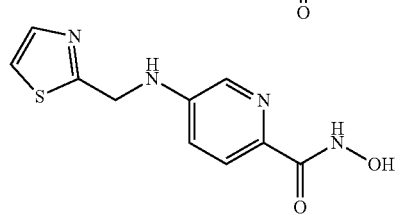

-continued

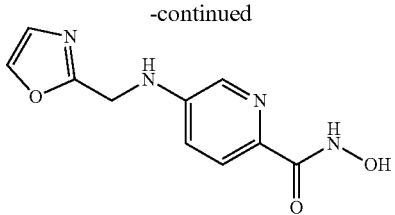

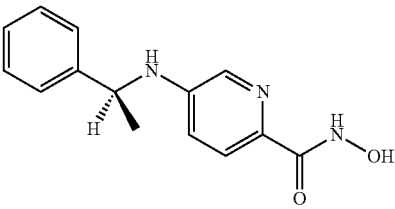

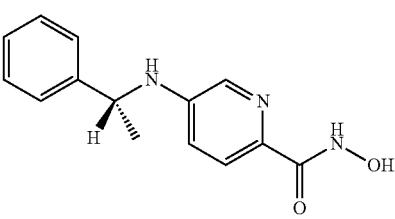

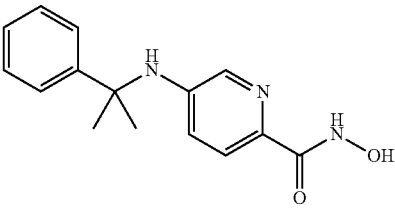

or pharmaceutically acceptable salts thereof; and
wherein the neurodegenerative disorder is Alzheimer's disease, Huntington's disease, frontotemporal dementia, progressive supranuclear palsy, cortcobasal dementia, Parkinson's with Lewy-Body dementia, post-traumatic neurodegeneration, or chronic traumatic encephalopathy.

7. The method of claim 6, wherein the neurodegenerative disorder is Alzheimer's disease.

\* \* \* \* \*

UNITED STATES PATENT AND TRADEMARK OFFICE
CERTIFICATE OF CORRECTION

PATENT NO. : 10,927,072 B2
APPLICATION NO. : 16/516747
DATED : February 23, 2021
INVENTOR(S) : John H. van Duzer Page 1 of 1

It is certified that error appears in the above-identified patent and that said Letters Patent is hereby corrected as shown below:

On the Title Page

Column 2, Line 8 under Other Publications please replace "Pittsburg" with "Pittsburgh."

In the Specification

In Column 2, Line 11 please replace "encorporated" with "incorporated."

In the Claims

In Claim 1, Column 36, Line 67 please replace "cortcobasal" with "corticobasal."

In Claim 6, Column 40, Line 44 please replace "cortcobasal" with "corticobasal."

Signed and Sealed this
Twenty-second Day of October, 2024

Katherine Kelly Vidal
*Director of the United States Patent and Trademark Office*